(12) United States Patent
Loeffler

(10) Patent No.: US 10,117,893 B2
(45) Date of Patent: Nov. 6, 2018

(54) THERAPEUTIC GAS FOR THE TREATMENT OF MITOCHONDRIAL DISORDERS

(75) Inventor: Bernd-Michael Loeffler, Berlin (DE)

(73) Assignee: Bernd-Michael Loeffler, Berlin (DE)

( * ) Notice: Subject to any disclaimer, the term of this patent is extended or adjusted under 35 U.S.C. 154(b) by 424 days.

(21) Appl. No.: 13/504,821

(22) PCT Filed: Oct. 27, 2010

(86) PCT No.: PCT/EP2010/066288
§ 371 (c)(1),
(2), (4) Date: Apr. 27, 2012

(87) PCT Pub. No.: WO2011/051357
PCT Pub. Date: May 5, 2011

(65) Prior Publication Data
US 2012/0213863 A1 Aug. 23, 2012

(30) Foreign Application Priority Data
Oct. 27, 2009 (DE) .......................... 10 2009 046 058

(51) Int. Cl.
| | | |
|---|---|---|
| *A61K 33/00* | (2006.01) | |
| *A61P 9/00* | (2006.01) | |
| *A61P 9/06* | (2006.01) | |
| *A61P 25/28* | (2006.01) | |
| *A61P 27/02* | (2006.01) | |
| *A61P 1/02* | (2006.01) | |
| *A61P 35/00* | (2006.01) | |
| *A61P 25/16* | (2006.01) | |
| *C01B 13/00* | (2006.01) | |
| *A61P 27/16* | (2006.01) | |
| *A61M 16/10* | (2006.01) | |

(52) U.S. Cl.
CPC ............. *A61K 33/00* (2013.01); *A61M 16/10* (2013.01); *A61M 16/101* (2014.02); *A61M 2016/1025* (2013.01); *A61M 2202/0208* (2013.01); *A61M 2230/205* (2013.01)

(58) Field of Classification Search
None
See application file for complete search history.

(56) References Cited

U.S. PATENT DOCUMENTS

| 5,792,090 | A | 8/1998 | Ladin | |
|---|---|---|---|---|
| 6,479,533 | B1 | 11/2002 | Yarosh | |
| 2006/0185669 | A1* | 8/2006 | Bassovitch | 128/202.12 |
| 2006/0281809 | A1 | 12/2006 | Miller et al. | |
| 2007/0072927 | A1* | 3/2007 | Vita et al. | 514/393 |
| 2009/0183738 | A1* | 7/2009 | Kostin et al. | 128/204.18 |

FOREIGN PATENT DOCUMENTS

| AU | 2005200728 A1 | 9/2006 |
|---|---|---|
| DE | 9208590 U1 * | 11/1992 |
| JP | 2006102037 A | 4/2006 |
| UA | 62415 A | 12/2003 |
| WO | 2008086025 A2 | 7/2008 |
| WO | 2008131070 A1 | 10/2008 |

OTHER PUBLICATIONS

Eckel (Eckel, R. H., et al., The metabolic syndrome, Lancet, 365 (2005) pp. 1415-1428).*
Carol Hutner: "Oxygen therapy for mitochondrial myopathy—Letter to the editor," (Jan. 10, 2002), http://the-medical-dictionary.com/myopathy_article_6.htm.
Julie Koziol: "International Symposium on Hyperbaric Oxygen Therapy Cutting Edge Forums and Ideas for Brain Injury", South Florida Hospital News and Healthcare Report, vol. 1, No. 1 (Jul. 27, 2004), http://southfloridahospitalnews.com/page/International_Symposium_on_Hyperbaric_Oxygen_Therapy_Offers_Cutting_Edge_Forums_and_Ideas_For_Brain_Injury/375/1/index.php.
K.R. Dave et al., "Hyperbaric oxygen therapy protects against mitochondrial dysfunction and delays onset of motor neuron disease in Wobbler mice," Neuroscience, vol. 120, No. 1, pp. 113-120 (Aug. 4, 2003).
Roberto Scatena et al., "Mitochondrial damage and metabolic compensatory mechanisms induced by hyperoxia in the U-937 cell line," Journal of Biochemistry and Molecular Biology, vol. 37, No. 4, pp. 454-459 (Jul. 31, 2004).
Re-Examination Report from Australian IP Office dated Nov. 18, 2014, in corresponding Australian Patent No. 2010311448.
Re-Examination Report from Australian IP Office dated Jul. 2, 2014, in corresponding Australian Patent No. 2010311448.
Re-Examination Report from Australian IP Office dated Feb. 17, 2014, in corresponding Australian Patent No. 2010311448.
Courtney, "Intermittent Hypoxic Training," International Wellbeing, 83 (Feb.-Mar. 2001).
Abstract of Gvozdjakova et al., "Coenzyme Q10 supplementation reduces corticosteroids dosage in patients with bronchial asthma," Biofactors, 25(1-4):235-40 (2005).
Gazdik et al., "Decreased levels of coenzyme Q10 in patients with bronchial asthma," Allergy, 57:811-814 (2002).
Abstract of Gazdik et al., "Levels of coenzyme Q10 in asthmatics," Bratisl Lek Listy, 103(10):353-6 (2002).
Trian et al., "Bronchial smooth muscle remodeling involves calcium-dependent enhanced mitochondrial biogenesis in asthma," JEM, 204(13):3173 (2007).

(Continued)

*Primary Examiner* — Bethany P Barham
*Assistant Examiner* — Dominic Lazaro
(74) *Attorney, Agent, or Firm* — Kriegsman & Kriegsman

(57) ABSTRACT

The use of gaseous oxygen for the production of a therapeutic gas for inhalation by a patient who has been identified as a person with a mitochondrial disorder or a coenzyme Q10 deficiency, for the treatment of mitochondrial disorders or Q10 deficiencies is disclosed.

For the first time a non-invasive method is disclosed, upon what the body's own level of Q10 can be raised significantly without further interventions.

5 Claims, No Drawings

(56) References Cited

OTHER PUBLICATIONS

Rosenfeldt et al., "Coenzyme Q10 therapy before cardiac surgery improves mitochondrial function and in vitro contractility of myocardial tissue," J. Thorac. Cardiovasc. Surg., 129:25-32 (2005).

Mitochondrial Medicine, edited by Salvatore DiMauro, Michio Hirano, and Eric A. Schon, published CRC Press, Chapter 1, "The mitochondrial respiratory chain and its disorders," (2006).

Explaining "Unexplained Illnesses" by Martin L. Pall, published CRC Press (2007).

Noh et al., "Inhibition of oxidative stress by coenzyme Q10 increases mitochondrial mass and improves bioenergetic function in optic nerve head astrocytes," Cell Death and Disease (2013) 4, e820; doi:10.1038/cddis.2013.341.

Abstract of Pancewicz et al., "Role of reactive oxygen species (ROS) in patients with erythema migrans, an early manifestation of Lyme borreliosis," Med. Sci. Monit., 7(6): 1230-5 (2001).

Pages 229-244 and 273-275 of Forensic Pathology, Second Edition, Vincent J. DiMaio and Dominick DiMaio, ISBN: 0-8493-0072-X (Jun. 28, 2001).

"Safety Advice: 3—Oxygen deficiency," The Linde Group, Linde AG, Seitnerstrasse 70, 82049 Pullach, Germany (2012).

"Oxygen Deficiency," European Industrial Gases Association (EIGA), Avenue des Arts 3-5, 1210 Brussels, Belgium (2002).

Berner et al., "A New Model for Atmospheric Oxygen over Phanerozoic Time," American Journal of Science, 289:333-361 (1989).

Zhang et al., "Hypoxia-inducible Factor 1-alpha (HIF-1-alpha)-mediated Hypoxia Increases BACE1 Expression and Beta-Amyloid Generation," The Journal of Biological Chemistry, 282(15):10873-10880 (2007).

Arkhipenko et al., "Adaption to Periodic Hypoxia and Hyperoxia Improves Resistance of Membrane Structures in Heart, Liver, and Brain," Bulletin of Experimental Biology and Medicine, 140(3):278-281 (2005).

Marriage et al., "Nutritional cofactor treatment in mitochondrial disorders," Journal of the American Dietetic Association, 103(8):1029-1038 (2003).

Duchen, "Section III: Mitochondria, Beta-Cell Function, and Type 2 Diabetes—Roles of Mitochondria in Health and Disease," Diabetes, 53(Suppl 1):S96-S102 (2004).

Abstract of Shinozawa et al., "Effect of biological membrane stabilizing drugs (coenzyme Q10, dextran sulfate and reduced glutathione) on adriamycin (doxorubicin)-induced toxicity and microsomal lipid peroxidation in mice," Gan To Kagaku Ryoho, 23(1): 93-8 (1996).

Abstract of Prokopov et al., "Intermittent Hypoxic Therapy/Training (IHT) as etiological and pathogenic anti-aging treatment," Sep. 6-10, 2007, at SENS3 conference, Queens' College, Cambridge, UK, retrieved online from http://www.sens.org/outreach/conferences/intermittent.

Mutschler, "Training in duenner Luft," Medical Sports Network, pp. 58-60 (2007).

Abstract of Loeffler et al., "Einfluss von Intervall-Hypoxie-Therapie-Plus auf mitochondriale Stoffwechsel Parameter and Herzfrequenzvariabilitaet," Oct. 29-30, 2010, Symposium Herzfrequenzvariabilitaet, Halle (Saale).

Douwes, "Die Prozesse des biologischen Alterns," Jun. 2010, Dr. Douwes informiert, Klinik St. George, pp. 1-7.

Abstract of Sacconi et al., "Coenzyme Q10 is frequently reduced in muscle of patients with mitochondrial myopathy," Neuromuscular Disorders, 20(1): 44-48 (Jan. 2010).

Galzachev et al., "Interval hypoxic-hyperoxic training in the treatment of the metabolic syndrome," Experimental & Clinical Gastroenterology, 7:51-56 (2010).

Abstract of Glazachev et al, "Combination hypo- and hyperoxic training in obesity associated psychosomatic disorders eatment and prevention," May 6-9, 2009, 17th European Congress on Obesity (ECO 2009), Amsterdam, The Netherlands.

\* cited by examiner

THERAPEUTIC GAS FOR THE TREATMENT OF MITOCHONDRIAL DISORDERS

The invention relates to the use of gaseous oxygen for the production of a therapeutic gas for inhalation by patients.

It is known that inhalation of oxygen-deficient air is used for the acclimatization of human bodies to high altitudes, particularly with regard to journeys of people to high mountain areas like the Himalayas or Tibet. But also athletes make use of this method which is known as altitude training to advance their physical ability in standard conditions.

The Interval-Hypoxia-Training (IHT) is a method of acclimatization to altitudes. In this process people inhale oxygen-deficient air (14-9% $O_2$) through a mask what initiates acclimatization activities in the body. Cyclical changes between oxygen-deficient air and ambient air make this altitude training highly efficient.

The Chronic fatigue syndrome (CFS) is a chronic disease which often causes invalidity. It is characterized by a paralyzing mental and corporal exhaustion/exhaustibility as well as by a specific combination of further symptoms. Beside chronic exhaustion, symptoms are, among others, headache, sore throat, joint and muscle pain, difficulties in concentration, disturbance of memory, less restful sleep, sensibility of lymph nodes as well as lasting debasement of fitness condition after exertion.

It is supposed, that CFS might be a result of mitochondrial disorders or oxidative stress, beside other unspecific diseases.

Oxidative stress is a metabolic status in which an amount of reactive oxygen species (ROS) is build or available, that is beyond the physiological levels. Those reactive oxygen species arise in line with metabolic processes of the mitochondrial electron transport chain and cytochrome-$P_{50}$-oxidases. These oxygen species are the peroxide anion radical $O_2^-$, hydrogen peroxide ($H_2O_2$) and hydroxyl radical OH (Schmidt R. F., e.a.: Physiologie des Menschen, Springer, 2007, p. 957 ff.).

Normal organism cells keep their ability to absorb reducing or oxidising substances alive by storing reserves of reducing or oxidising substances. An imbalance between these pools, which overcharges the normal function of repair and detoxication of cells and therefore causes a damage of all cellular and extracellular macromolecules, is called oxidative stress (David Heber, George L. Blackburn, Vay Liang W. Go, John Milner (Ed.): Nutritional Oncology. Academic Press, 2006. p. 314).

A possible treatment of this disease consists in application of Q10 (ubiquinone). Ubiquinone (also named UQ, coenzyme Q, CoQ, Q or coenzyme $Q_{10}$) is a quinone derivative with a lipophilic isoprenoid side chain, structurally related to vitamin K and vitamin E. The reduced phenolic form is called ubihydrochinone or ubiquinol ($QH_2$). Q10, coenzyme Q, is an essential vector of electrons and protons between complex I and complex II, respectively, and complex III of the respiratory chain.

Some deficiency symptoms of Q10 also appearing may have different reasons.

The current most known situation of reduction of Q10 by medication is administration of statines to decrease the cholesterol level and LDL. The synthesis of mevalonic acid gets blocked, which is a collective junction for the production of cholesterol or Q10. Consequences for the patients are partly extensive: muscle pain, restricted walking distance comparable to intermittent claudication, general faintness, tiredness. They are generally not worked therapeutically with.

There is a raising amount of different indications known for lowered Q10, and for giving significant amendments by substitution of Q10 to "therapeutic" Q10 serum level. These are, among others, cardiac insufficiency, migraine, tinnitus. Further there are correlations between lower Q10 levels and cancer, Q10 and immune system and depressions.

The Q10 level is different in various organs and the highest levels are found in myocardial muscle cells. Q10 declines by raising age. Generally it is assumed that Q10 is no vitamin because the body is able to produce enough Q10 by self synthesis. But this is apparently in many situations not the case (e.g. chronic diseases), but also in "as healthy known probands" one can find extensive lowered levels of Q10, without an apparent external cause. The standard value of Q10 is 0.8-1.15 mg/l, the preventive medical rated range is >1.4 mg/l, the therapeutic area is >2.5 mg/l.

The object of the invention is providing means to medicate mitochondrial disorders and to elevate the concentration of Q10 in plasma of patients.

The object is solved by use of gaseous oxygen for the production of a therapeutic gas for inhalation according to the main claim.

Thus the object is solved by use of gaseous oxygen for the production of a therapeutic gas for inhalation by a patient who has been identified as a person with a mitochondrial disorder or a Q10 deficiency, for the treatment of mitochondrial disorders or the Q10 deficiencies.

According to the invention the use is preferred, in which the inhalation of the therapeutic gas is performed in at least two sections.

Especially preferred is the use according to the present invention wherein the concentration of the oxygen in the therapeutic gas has a different amount in the respective sections.

Especially preferred is the use according to the present invention wherein the concentration of the oxygen in the therapeutic gas is from about 15 Vol-% to about 9 Vol-%.

Especially preferred is the use according to the present invention wherein the concentration of the oxygen in the therapeutic gas is from about 30 Vol-% to about 55 Vol-%.

According to the present invention the use is especially preferred wherein the respective sections of inhalation last from 1 minute up to 60 minutes.

Furthermore according to the invention the use is especially preferred wherein the total time of inhalation lasts from 10 minutes up to 5 hours.

Also preferred is the use wherein the oxygen partial pressure in the patient is detected during inhalation.

Exceptionally preferred is the use wherein the mitochondrial disorder or the Q10 deficiency to be treated is associated with: cardiac insufficiency, arrhythmias, cardiac arrest, tinnitus, acute hearing loss, senile ablepsia, age-related macular degeneration, parodontitis, gingivitis, cancer, solid tumour, Attention Deficit/hyperactivity Disorder (ADHD), autism, Attention Deficit Disorder (ADD), parkinsonism, dementia, Alzheimer's disease, olfactory disorders, migraine, neuropathic pain, pruritis, asthma, chronic obstructive pulmonary disease (COPD), apnoea, dialysis, apheresis, incontinence, neurodermatitis, psoriasis, wound healing, type 2 diabetes, overweight, obesity, metabolic syndrome, multiple sclerosis, allergy.

An especially preferred use according to the present invention is to elevate or increase the plasma levels of coenzyme Q10 in a patient.

In other words, the main object of the invention is to provide a method for the treatment of a patient having mitochondrial disorders or coenzyme Q10 deficiencies, and that the method consists of administering a therapeutic gas to the patient, and that the therapeutic gas contains different levels of oxygen, forming either a hypoxic or a hyperoxic therapeutic gas that is administered to the patient in a regime, in which the level is changed from one section to the other from hypoxic to hyperoxic and back to hypoxic and so on.

The "Intermittent Hypoxia-Hyperoxia-Therapy" (IHHT), as it is called by the inventor, is a new therapy method that can be used for a wide range of diseases that are correlated with mitochondrial disorders and/or coenzyme Q10 deficiencies.

In the art there are methods known as intermittent hypoxia ("Intermittent Hypoxia: From Molecular Mechanism To Clinical Applications"; Lei Xi and Tatiana V Serebrovskaja (Eds.) 2009 Nova Science Publishers Inc. New York). The main difference to known methods (Diving: Normoxia with Hypoxia and simultaneous Hypercapnia (elevation of $CO_2$ levels in blood); von Ardenne method: Normoxia Hyperoxia, method with ozone (Normoxia-Ozone); so-called Hypobaric Hypoxia: Hypoxia with simultaneous pressure reduction of the air to breath) is that a normobaric hypoxia (15-9% $O_2$) hyperoxia (30-55% $O_2$) method is used.

Furthermore, Hypoxia is described in the art as a dangerous principle as the method is compared to obstructive-sleep-apnoea (OSA). In contrast, OSA differs from IHHT, in that the intervals and the duration of Hypoxia sections are regulated.

Surprisingly it was found, that the concentration of Q10 raises in the blood of the patients, if cycles of inhalation of hypoxygenic and hyperoxygenic gases follow each other. Thereby it is advantageous to carry out these cycles several times following successively one after the other and thereby forming a session and repeating the complete session in predefined intervals.

For the first time a non-invasive method is disclosed, whereby the body's own level of Q10 can be raised significantly without further interventions or medications. Up to now it was only possible to elevate the plasma levels by administering Q10 orally or parenterally to a patient in need of such a medication.

By using cycles of inhalation of hypoxygenic and hyperoxygenic gases it is possible to elevate the plasma levels of Q10 in a patient up to the therapeutic range of 2.5 mg/l without any problem.

As the plasma level of coenzyme Q10 is believed to be highly related with many diseases of the heart, brain, eyes, lungs, bladder, kidneys, skin, nervous system, sense of hearing, and also with pain and cancer, it is a great advantage to elevate the plasma level in a patient without external administration of the coenzyme Q10. The body's-own production of coenzyme Q10 is stimulated by the inhalation of hypoxygenic and hyperoxygenic gases.

Further it was found that by a capable oral therapy with so-called "mitogen substances" (e.g. acetyl salicylic acid, vitamins, alpha liponic acid, minerals, Zn, Mn, etc.) the effect of the oral therapy with Q10 can be clearly amplified. Consequently, the same applies to the method of the invention so that co-medication with mitogen substances may be carried out.

It is apparent from the description of the invention that the levels of oxygen in the respective hypoxygenic and hyperoxygenic gases may be adjusted and easily optimized for a certain disease. It is possible for a skilled artesian to optimize those levels using the teaching of the present invention without deviating from the scope of the claims given herein.

The following examples explain the invention in greater detail.

EXAMPLE 1

18 test persons were chosen and concluded the test. The test persons get randomized after an initial check-up into a control group (N=8) and a treatment group (N=10). Within three weeks all of the test persons graduated ten inhalation proceedings of 36 minutes in each case. The persons belonging to the control group respired ambient air through an air supply tube of the respiration apparatus (tube not connected), the treatment group respired for 6 minutes 12 Vol.-% $O_2$, afterwards for 3 minutes 44 Vol.-% $O_2$. This cycle was repeated three times, so that altogether four cycles were completed, forming an inhalation session of 36 minutes. The lowest value for $pCO_2$ was defined to 80%.

After completion of the ten treatment units all test persons were examined again.

The inhalation was arranged by using an ordinary respiration apparatus. Analogous apparatus are known from the IHT. Those apparatuses were accordingly modified, so that next to hypoxygenic gases also hyperoxygenic gases with an oxygen content of 30-55 Vol-% can be ventilated.

Monitoring of oxygen partial pressure of the test persons blood was performed using a commercially available equipment as for example given in DE 92 08 590 U1.

The results of the collected physiological parameters of the test persons are presented in Table 1. The values of NPE (3-nitro phenyl acetic acid) and citrulline have been measured in the urine, the values for MMS (methyl malonic acid), Q10 (coenzyme $Q_{10}$), and Mito Act (mitochondrial activity) in the blood of the test persons.

TABLE 1

| Parameter | | Control group | | | Treatment group | | | uTT |
|---|---|---|---|---|---|---|---|---|
| | | Mean | SD | pTT | Mean | SD | pTT | |
| NPE | before | 7.52 | 11.70 | 0.37 | 10.09 | 15.17 | 0.244 | |
| | after | 29.05 | 71.17 | | 33.11 | 46.57 | | |
| Citrulline | before | 5.89 | 3.39 | 0.94 | 8.29 | 9.59 | 0.845 | |
| | after | 5.38 | 6.05 | | 7.59 | 4.46 | | |
| MMS | before | 0.94 | 0.46 | 0.25 | 1.02 | 1.37 | 0.325 | |
| | after | 1.05 | 0.33 | | 0.53 | 0.33 | | |
| Q10 | before | 0.78 | 0.26 | 0.02 | 0.96 | 0.31 | 0.000 | 0.23 |
| | after | 0.91 | 0.31 | | 1.37 | 0.35 | | 0.02 |
| Mito Act | before | 86.28 | 12.41 | 0.16 | 84.74 | 6.59 | 0.004 | 0.77 |
| | after | 94.03 | 5.14 | | 94.57 | 4.31 | | 0.84 |

Statistical analysis:
Mean: Mean value
SD: Standard deviation.
pTT: paired T-Test, 2-tailed for unequally variance of the groups within the groups for indicated values before/after treatment.
uTT: unpaired T-Test between treatment group and control group.

EXAMPLE 2

A patient showing symptomatic disorders caused by chronic borreliosis was treated 1 minute with 13 Vol-% hypoxia and 9 minutes with 38 Vol-% hyperoxia in 6 cycles forming a session of one hour duration.

A significant improvement of the skin structure and the aspect of the skin was achieved after 10 sessions. The improvement remained for about 3 months.

The invention claimed is:

1. A method for the treatment of mitochondrial disorders or coenzyme Q10 deficiencies, the method comprising:
   a) identifying a person with a mitochondrial disorder or a coenzyme Q10 deficiency; and
   b) administering to the person via inhalation a therapeutic gas comprising gaseous oxygen in the form of an intermittent hypoxia-hyperoxia therapy, wherein sessions of inhalation of hypoxygenic and hyperoxygenic gases alternate and wherein the concentration of oxygen in the therapeutic gas is from about 15 Vol-% to about 9 Vol-% for a hypoxia session;
   wherein inhalation of the gas is performed in at least two time sessions, one of the time sessions being a hypoxia session of 6 minutes in which the concentration of oxygen in the therapeutic gas is 12 Vol-% and another of the time sessions being a hyperoxia session of 3 minutes in which the concentration of the oxygen in the therapeutic gas is 44 Vol-% and wherein the inhalation of the therapeutic gas results in an increase of coenzyme Q10 to a therapeutic range of 2.5 mg/l in plasma of the person.

2. A method for the treatment of mitochondrial disorders or coenzyme Q10 deficiencies, the method comprising:
   a) identifying a person with a mitochondrial disorder or a coenzyme Q10 deficiency; and
   b) administering to the person via inhalation a therapeutic gas comprising gaseous oxygen in the form of an intermittent hypoxia-hyperoxia therapy, wherein sessions of inhalation of hypoxygenic and hyperoxygenic gases alternate and wherein the concentration of oxygen in the therapeutic gas is from about 15 Vol-% to about 9 Vol-% for a hypoxia session;
   wherein inhalation of the gas is performed in at least four cycles, each cycle comprising a hypoxia session of 6 minutes in which the concentration of oxygen in the therapeutic gas is 12 Vol-% followed by a hyperoxia session of 3 minutes in which the concentration of the oxygen in the therapeutic gas is 44 Vol-% and wherein the inhalation of the therapeutic gas results in an increase of coenzyme Q10 to a therapeutic range of 2.5 m/11 in plasma of the person.

3. A method for the treatment of mitochondrial disorders or coenzyme Q10 deficiencies, the method comprising:
   a) identifying a person with a mitochondrial disorder or a coenzyme Q10 deficiency; and
   b) administering to the person via inhalation a therapeutic gas comprising gaseous oxygen in the form of an intermittent hypoxia-hyperoxia therapy, wherein sessions of inhalation of hypoxygenic and hyperoxygenic gases alternate and wherein the concentration of oxygen in the therapeutic gas is from about 15 Vol-% to about 9 Vol-% for a hypoxia session;
   wherein inhalation of the gas is performed in at least two time sessions, one of the time sessions being a hypoxia session of 1 minute in which the concentration of oxygen in the therapeutic gas is 13 Vol-% and another of the time sessions being a hyperoxia session of 9 minutes in which the concentration of the oxygen in the therapeutic gas is 38 Vol-% and wherein the inhalation of the therapeutic gas results in an increase of coenzyme Q10 to a therapeutic range of 2.5 m/11 in plasma of the person.

4. A method for the treatment of mitochondrial disorders or coenzyme Q10 deficiencies, the method comprising:
   a) identifying a person with a mitochondrial disorder or a coenzyme Q10 deficiency; and
   b) administering to the person via inhalation a therapeutic gas comprising gaseous oxygen in the form of an intermittent hypoxia-hyperoxia therapy, wherein sessions of inhalation of hypoxygenic and hyperoxygenic gases alternate and wherein the concentration of oxygen in the therapeutic gas is from about 15 Vol-% to about 9 Vol-% for a hypoxia session;
   wherein inhalation of the gas is performed in at least six cycles, each cycle comprising a hypoxia session of 1 minute in which the concentration of oxygen in the therapeutic gas is 13 Vol-% followed by a hyperoxia session of 9 minutes in which the concentration of the oxygen in the therapeutic gas is 38 Vol-% and wherein the inhalation of the therapeutic gas results in an increase of coenzyme Q10 to a therapeutic range of 2.5 mg/l in plasma of the person.

5. A method for the treatment of mitochondrial disorders or coenzyme Q10 deficiencies, the method comprising:
   a) identifying a person with a mitochondrial disorder or a coenzyme Q10 deficiency; and
   b) administering to the person via inhalation a therapeutic gas comprising gaseous oxygen in the form of an intermittent hypoxia-hyperoxia therapy, wherein sessions of inhalation of hypoxygenic and hyperoxygenic gases alternate and wherein the concentration of oxygen in the therapeutic gas is from about 15 Vol-% to about 9 Vol-% for a hypoxia session;
   wherein the concentration of the oxygen in the therapeutic gas is about 55 Vol-% for a hyperoxia session and wherein the inhalation of the therapeutic gas results in an increase of coenzyme Q10 to a therapeutic range of 2.5 mg/l in plasma of the person.

\* \* \* \* \*